United States Patent
Hedrick et al.

(10) Patent No.: US 12,128,063 B2
(45) Date of Patent: Oct. 29, 2024

(54) BIOCOMPATIBLE AND BIODEGRADABLE ANTIVIRAL POLYMERS

(71) Applicants: International Business Machines Corporation, Armonk, NY (US); Agency for Science, Technology and Research, Singapore (SG)

(72) Inventors: James L. Hedrick, Pleasanton, CA (US); Yi Yan Yang, Singapore (SG); Agnes Mari Kuroki, Singapore (SG); Jiayu Eunice Leong, Singapore (SG); Wei Ping Eddy Tan, Singapore (SG)

(73) Assignee: International Business Machines Corporation, Armonk, NY (US)

( * ) Notice: Subject to any disclaimer, the term of this patent is extended or adjusted under 35 U.S.C. 154(b) by 157 days.

(21) Appl. No.: 17/494,708

(22) Filed: Oct. 5, 2021

(65) Prior Publication Data

US 2023/0122378 A1    Apr. 20, 2023

(51) Int. Cl.
*A61K 31/795* (2006.01)
*A61P 31/14* (2006.01)
*C08G 64/02* (2006.01)

(52) U.S. Cl.
CPC ............ *A61K 31/795* (2013.01); *A61P 31/14* (2018.01); *C08G 64/025* (2013.01)

(58) Field of Classification Search
CPC .................................................... A61K 31/795
See application file for complete search history.

(56) References Cited

U.S. PATENT DOCUMENTS

| | | | |
|---|---|---|---|
| 5,462,751 A | 10/1995 | Kossovsky et al. |
| 9,737,615 B2 | 8/2017 | Castillo et al. |
| 9,795,668 B2 | 10/2017 | Jain et al. |
| 2002/0071843 A1 | 6/2002 | Li et al. |
| 2013/0280204 A1 | 10/2013 | Weight et al. |
| 2021/0154308 A1 | 5/2021 | Davis et al. |

FOREIGN PATENT DOCUMENTS

EP         2499248 B1      1/2017

OTHER PUBLICATIONS

Rokicki (Prog. Polym. Sci. 25 (2000) 259-342). (Year: 2000).*

(Continued)

*Primary Examiner* — Benjamin J Packard
(74) *Attorney, Agent, or Firm* — Stosch Sabo

(57) ABSTRACT

A water-soluble polymer having an aliphatic polycarbonate backbone, a first carbonate monomer with at least one hydrophilic functionality, and a second carbonate monomer with at least one hydrophobic functionality is able to completely and quickly eliminate a virus from a human and/or animal cell. The at least one hydrophilic functionality is a sulfate, a sulfonate, a carboxylate, and/or a phosphate and the at least one hydrophobic functionality is an alkyl. The hydrophilic/hydrophobic functionalities of the polymer may be tuned to enhance the antiviral properties of the polymer and/or to decrease any cytotoxicity associated with the application of the polymer to a human and/or animal cell. The antiviral polymer is biocompatible and biodegradable.

17 Claims, 11 Drawing Sheets

$IC_{50}$ values for NTCP-HepG2 cells treated with pS30, pS50 and pS80

(56) References Cited

OTHER PUBLICATIONS

Alasino et al., Characterization of the Inhibition of Enveloped Virus Infectivity by the Cationic Acrylate Polymer Eudragit E100, Macromolecular Bioscience 7:1132-1138 (2007).
Andronova & Albertsson, Resilient Bioresorbable Copolymers Based on Trimethylene Carbonate, L-Lactide, and 1,5-Dioxepan-2-one, Biomacromolecules 7:1489-1495 (2006).
Baba et al., Mechanism of inhibitory effect of dextran sulfate and heparin on replication of human immunodeficiency virus in vitro, Proc. Natl. Acad. Sci. USA 85:6132-6136 (1988).
Bhatia et al., Linear polysialoside outperforms dendritic analogs for inhibition of influenza virus infection in vitro and in vivo, Biomaterials 138:22-34 (2017).
Bianculli et al., Antiviral Polymers: Past Approaches and Future Possibilities, Macromolecules 53:9158-9186 (2020).
Chen et al., Advanced drug and gene delivery systems based on functional biodegradable polycarbonates and copolymers, Journal of Controlled Release 190:398-414 (2014).
Cushman et al., Preparation and Anti-HIV Activities of Aurintricarboxylic Acid Fractions and Analogues: Direct Correlation of Antiviral Potency with Molecular Weight, J. Med. Chem. 34(1):329-337 (1991).
Fitzgerald & Weiss, Synthesis, Properties, and Structure of Sulfonate Ionomers, Polymer Reviews 28(1):99-185 (1988).
Gunther et al., Antiviral potential of 3'-sialyllactose- and 6'-sialyllactose-conjugated dendritic polymers against human and avian influenza viruses, Scientific Reports 10:768 (pp. 1-9) (2020).
Haldar et al., Bifunctional Polymeric Inhibitors of Human Influenza A Viruses, Pharmaceutical Research 27 (2):259-263 (2010).
Chiyama et al., Sulfated Polysaccharide, Curdlan Sulfate, Efficiently Prevents Entry/Fusion and Restricts Antibody-Dependent Enhancement of Dengue Virus Infection In Vitro: A Possible Candidate for Clinical Application, PLOS Neglected Tropical Disease 7(4):e2188 (pp. 1-17) (2013).
Jung et al., Acid- and base-catalyzed hydrolyses of aliphatic polycarbonates and polyesters, Catalysis Today 115:283-287 (2006).
Korner et al., of Mice and Men: The Coronavirus MHV and Mouse Models as a Translational Approach to Understand SARS-CoV-2, Viruses 12:880 (pp. 1-26) (2020).
Kricheldorf & Rost, Biodegradable Multiblock Copolyesters Prepared from e-Caprolactone, L-Lactide, and Trimethylene Carbonate by Means of Bismuth Hexanoate, Macromolecules 38:8220-8226 (2005).
Mammen et al., Effective Inhibitors of Hemagglutination by Influenza Virus Synthesized from Poisoners Having Active Ester Groups. Insight into Mechanism of Inhibition, J. Med. Chem. 38(21):4179-4190 (1995).
Nederberg et al., Organocatalytic Ring Opening Polymerization of Trimethylene Carbonate, Biomacromolecules 8:153-160 (2007).
Pratt et al., Exploration, Optimization, and Application of Supramolecular Thiourea-Amine Catalysts for the Synthesis of Lactide (Co)polymers, Macromolecules 39:7863-7871 (2006).
Savage et al., Anti-HIV Activities of Precisely Defined, Semirigid, Carboxylated Alternating Copolymers, J. Med. Chem. 57:6354-6363 (2014).
Schandock et al., Macromolecular Antiviral Agents against Zika, Ebola, SARS, and Other Pathogenic Viruses, Adv. Healthcare Mater. 6:1700748 (pp. 1-14) (2017).
Spoden et al., Polyethylenimine is a Strong Inhibitor of Human Papillomavirus and Cytomegalovirus Infection, Antimicrobial Agents and Chemotherapy, 56(1):75-82 (2012).
Suriano et al., Functionalized cyclic carbonates: from synthesis and metal-free catalyzed ring-opening polymerization to applications, Polym. Chem. 2:528-533 (2011).
Tan et al., Overcoming Barriers in Polycarbonate Synthesis: A Streamlined Approach for the Synthesis of Cyclic Carbonate Monomers, Macromolecules 54:1767-1774 (2021).
Tang et al., Antiviral Agents from Multivalent Presentation of Sialyl Oligosaccharides on Brush Polymers, ACS Macro Lett. 5:413-418 (2016).
Theodoropoulos et al., Sulfone-type crosslinks in sulfonation of macronet polystyrene backbone, Polymer 34 (18):3905-3910 (1993).
Ulery et al., Biomedical Applications of Biodegradable Polymers, Journal of Polymer Science Part B: Polymer Physics 49:832-864 (2011).
Jmemura et al., Design of a Sialylglycopolymer with a Chitosan Backbone Having Efficient Inhibitory Activity against Influenza Virus Infection, J. Med. Chem. 51(15):4496-4503 (2008).
Wang et al., Cationic Phenylene Ethynylene Polymers and Oligomers Exhibit Efficient Antiviral Activity, ACS Appl. Mater. Interfaces 3:2209-2214 (2011).
Witvrouw & De Clercq, Sulfated Polysaccharides Extracted from Sea Algae as Potential Antiviral Drugs, Gen. Pharmac. 29(4):497-511 (1997).
Ekblad et al. "A highly lipophilic sulfated tetrasaccharide glycoside related muparfostat (PI-88) exhibits virucidal activity against herpes simplex virus," ScienceDirect Antiviral Research, May 2010, pp. 196-203, vol. 86, Issue 2.
Ichiyama, et al., "Cooperative Orthogonal Macromolecular Assemblies with Broad Sprectrum Antiviral Activity, High Selectivity, and Resistance Mitigation," Macromolecules, Mar. 17, 2016, 9 pages, vol. 49, Issue 7.
Lee et al., "Antiviral effect of the heparan sulfate mimetic, PI-88, against dengue and encephalitic flaviviruses," Elsevier Antiviral Research, 2006, pp. 31-38, vol. 69.
Nakashima, et al., "Sulfation of Polysaccharides Generates Potent and Selective Inhibitors of Human Immuno-Deficiency Virus Infection and Replication In Vitro," Jpn. J. Cancer Res. (Gann), Nov. 1987, pp. 1164-1168, vol. 78.
Pujol et al., "Natural Sulfated Polysaccharides for the Prevention and Control if Viral Infections," Top Heterocycl Chem, Jul. 4, 2007, pp. 259-281.

\* cited by examiner

BIOCOMPATIBLE AND BIODEGRADABLE ANTIVIRAL POLYMERS

TECHNICAL FIELD

The present invention relates generally to antiviral agents, and more specifically to biocompatible and biodegradable sulfonated polycarbonate polymers with broad spectrum antiviral properties.

BACKGROUND OF THE INVENTION

Viral diseases continue to be one of the leading causes of morbidity and mortality since ancient times. In recent years, viral infections have emerged as an eminent global public health problem mainly because of a rapid increase in human population, aging, global warming, and medical treatments that suppress the immune system, the latter including irradiation therapy, anti-cancer chemotherapy, and organ transplantation. For example, the SARS outbreak of 2003, the COVID-19 outbreak of 2019, and the dengue virus (DENV), and the bird flu (e.g. H1N1) outbreaks have imposed enormous economic burdens on societies throughout the world. Other viruses that have been found in human populations include Nipah virus, the Chikungunya (CHIKV) virus, the Marburg virus (MARV), and a mutated avian influenza A(H7N9) virus. In West Africa, the detrimental Ebolavirus (EBOV) has become an epidemic resulting in the loss of more than eleven thousand lives. While significant effort has been directed to develop vaccines and antiviral drugs to control and eradicate viral infections, the rapid mutation of viruses, due to inherent genomic instability, makes vaccinations inefficient. Moreover, for many viral infections (e.g., DENV, CHIKV, MARV, and EBOV), there are currently no antiviral drugs available to treat the infections. Since there are so many types and subtypes of pathogenic viruses, particularly RNA viruses that easily mutate to form drug-resistant strains, it is impractical to deal with each virus individually. Treatment of viral infections continues to be elusive owing to the variance in virus structure (RNA, DNA, enveloped and non-enveloped viruses) together with their ability to rapidly mutate and garner resistance.

SUMMARY OF THE INVENTION

In one aspect, the present invention relates to composition comprising a water-soluble polymer with an aliphatic polycarbonate backbone, a first carbonate monomer with at least one hydrophilic functionality; and a second carbonate monomer with at least one hydrophobic functionality.

In another aspect, the present invention relates to a composition comprising a water-soluble polymer with an aliphatic polycarbonate backbone, at least one carbonate monomer with a hydrophilic sulfonate group, and at least one carbonate monomer with a hydrophobic alkyl group.

In a further aspect, the present invention relates to a method for inhibiting viral infections in a human or animal subject comprising: obtaining a composition comprising a water-soluble polymer with an aliphatic polycarbonate backbone, a first carbonate monomer with at least one hydrophilic functionality, and a second carbonate monomer with at least one hydrophobic functionality; and administering the composition to a human and/or animal subject for inhibiting viral infections in the human and/or animal subject.

Additional aspects and/or embodiments of the invention will be provided, without limitation, in the detailed description of the invention that is set forth below.

DETAILED DESCRIPTION OF THE INVENTION

Figure 1:
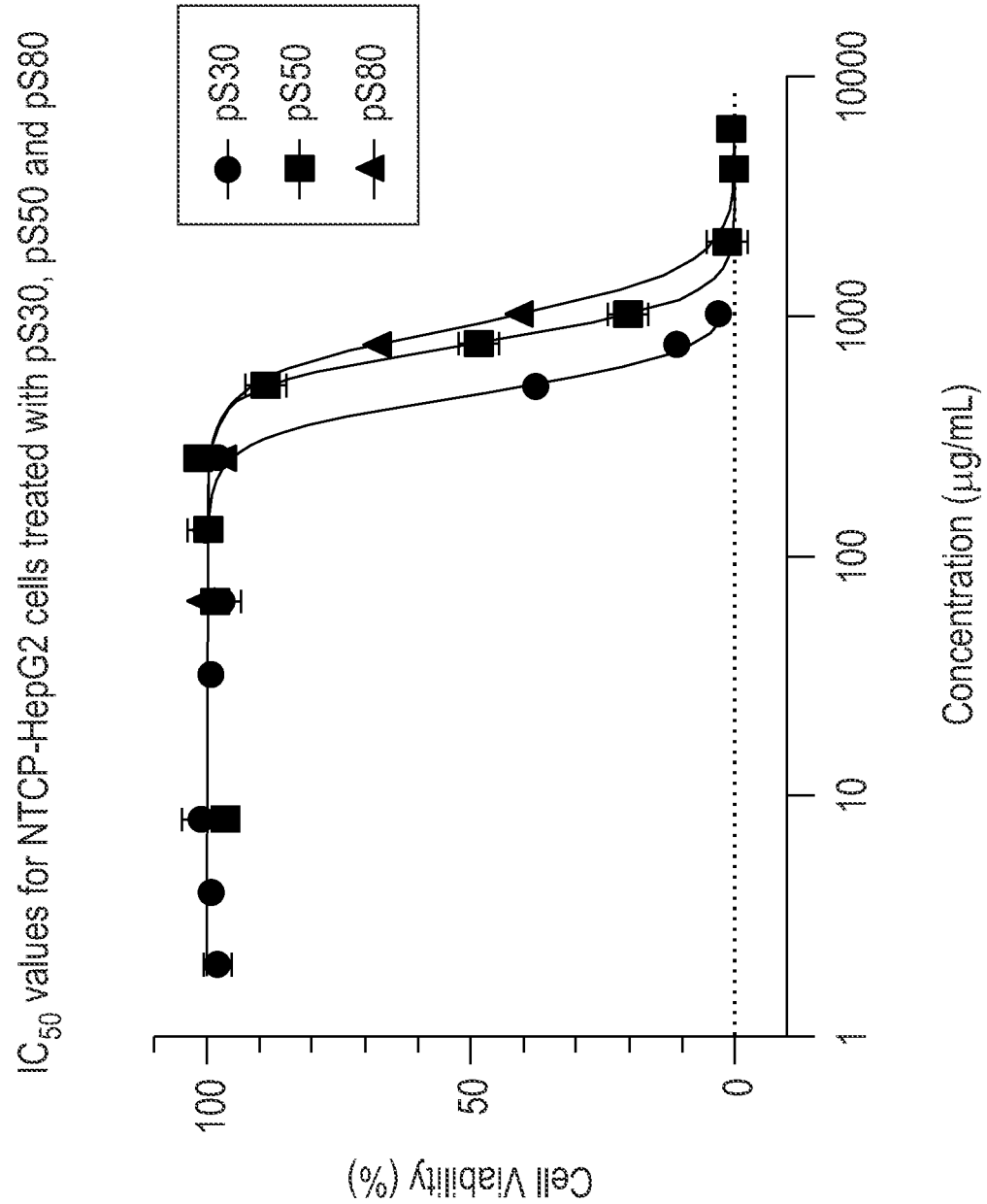
FIG. 1 is a toxicity data graph that shows the percentage of cell viability of NTCP-HepG2 cells exposed for 24 hours at 37° C. to various concentrations (ranging from ~2 µg/mL to 10 mg/mL) of the antiviral polymers, pS30, pS50, and pS80.

Set forth below is a description of what are currently believed to be preferred aspects and/or embodiments of the claimed invention. Any alternates or modifications in function, purpose, or structure are intended to be covered by the appended claims. As used in this specification and the appended claims, the singular forms "a," "an," and "the" include plural referents unless the context clearly dictates otherwise. The terms "comprise," "comprised," "comprises," and/or "comprising," as used in the specification and appended claims, specify the presence of the expressly recited components, elements, features, and/or steps, but do not preclude the presence or addition of one or more other components, elements, features, and/or steps.

As used herein, the term "polymer" refers to a macromolecule composed of repeating units of monomers that are linked via covalent bonds. Examples of polymers include homopolymers, which have a single monomer repeating unit, and copolymers, which have a polymer with more than one monomer species. Within the context of the present invention, the antiviral agents described herein are referred to interchangeably as copolymers and polymers.

As used herein, the term "alkyl" refers to a chemical functionality with the general formula $C_nH_{2n+1}$. Examples of alkyls include, without limitation, methyl (CH$_3$·), ethyl (C$_2$H$_5$·), propyl (C$_3$H$_7$·), butyl (C$_4$H$_9$·), pentyl (C$_5$H$_{11}$·), hexyl (C$_6$H$_{13}$·), heptyl (C$_7$H$_{15}$·), octyl (C$_8$H$_{17}$·), nonyl (C$_9$H$_{19}$·), decyl (C$_{10}$H$_{21}$·), undecyl (C$_{11}$H$_{23}$·), and dodecyl (C$_{12}$H$_{25}$·). The alkyls may have any skeletal formula, which is identified through the use of an appropriate prefix. For example, the alkyl functional group may be normal (n-; example n-butyl), secondary (sec-; example sec-butyl), tertiary (tert-; example tert-butyl), or an isomer (iso-; example isobutyl). Alkyl groups are non-polar hydrophobic groups.

As used herein, the term "aliphatic" refers to carbon atoms that form open chains.

As used herein, the term "biodegradable" refers to a compound that may be broken down into carbon dioxide, water vapor, and organic material.

As used herein, the term "biocompatible" refers to a compound that is not harmful to living tissue.

Viruses can be classified as (i) RNA and DNA viruses, based on their genomes, and (ii) enveloped and non-enveloped viruses, based on whether the viral particles are wrapped in a host-derived membrane or not. Examples of RNA viruses include, without limitation, influenza, DENV, CHIKV, MARV, EBOV, and Enterovirus 71 (EV71). One non-limiting example of a DNA virus is herpes simplex virus (HSV). Examples of enveloped viruses include, without limitation, DENV, CHIKV, MARV, EBOV, HSV, and influenza. One non-limiting example of a non-enveloped virus is EV71. The difference between RNA, DNA, enveloped, and non-enveloped viruses prevents the design of a general solution for prevention and treatment of viral infections.

Most emerging and re-emerging viruses are RNA viruses. RNA viruses infect cells through interactions between virus surface proteins and cell surface receptors followed by endocytosis internalization wherein the viral and cellular membranes fuse and assemble into virions. A single virus particle can infect a cell through one or multiple cell surface receptors. Examples of cell surface receptors on enveloped and non-enveloped RNA viruses include, without limitation, (i) T-cell immunoglobulin and mucin domain (TIM-1/TIM-3) proteins (e.g., EBOV, MARV, and DENV); (ii) haparan sulfate proteoglycans (e.g., DENV, HSV and EV71); and (iii) sialic acid (e.g., EV71 and influenza). Once a cell is infected, the virion delivers its DNA or RNA genome into the host cell where the viral genome is replicated. Once the new viral particles mature within the host cell, the progeny virions are released from the host cell through rupture of the host cell or gradual extrusion through the cell membrane. Once released, newly formed progeny virions spread the infection from cell to cell. Over time, RNA viruses are known to mutate. In this regard, antiviral agents that are effective against one viral genome will not necessarily work against the mutated viral genome.

The antiviral polymers described herein are (i) have a broad therapeutic window, (ii) are water-soluble and non-cytotoxic, (iii) have a biocompatible and biodegradable backbone, (iii) have tunable moieties that provide the polymers with a hydrophilic/hydrophobic balance, and (iv) are highly active at low concentrations.

The present invention provides sulfonated polycarbonate polymers with broad spectrum antiviral properties that are able to completely and quickly eliminate a virus from a human and/or animal cell. The antiviral polymers act by forming a complex with viral surface proteins thus preventing the viruses from binding to cell surface receptors. Unlike existing antiviral agents, which attempt to kill a virus through target specificity, the antiviral polymers described herein selectively stop the replication of the viral genome, thus, mitigating the drug resistance that is inherent with currently used antiviral agents. The broad-spectrum capability of the antiviral polymers means that they are not specific to a particular type of virus and are capable of stopping replication of all viruses, including RNA-based, DNA-based, enveloped, and non-enveloped viruses.

In one embodiment, the antiviral polymer is a water-soluble polymer comprising an aliphatic polycarbonate backbone. As the carbonate bonds in the aliphatic polycarbonate backbone are facile and do not include any bulky phenyl groups and/or stiff chains, the antiviral polymers described herein are readily biodegradable with enzymes or other compounds that can reach and degrade the polycarbonate backbone into organic compounds that are not harmful to an organism and/or the environment.

In another embodiment, the water-soluble antiviral polymer has at least one anionic hydrophilic functionality and at least one hydrophobic carbonate monomer comprising an alkyl functional group. Examples of anionic hydrophilic functional groups include, without limitation, sulfates, sulfonates, carboxylates, and phosphates. In a further embodiment, the water-soluble polymer has at least one hydrophobic functionality. As is known to those of skill in the art, partially hydrophobic polymers maintain their water-solubility. The hydrophilic/hydrophobic functionalities of the polymer may be tuned to enhance the antiviral properties of the polymer and/or to increase the biocompatibility of the polymers by decreasing any cytotoxicity associated with the application of the polymer to a human and/or animal cell. In another embodiment, the water-soluble antiviral polymer comprises an aliphatic polycarbonate backbone with at least one hydrophilic sulfonate functional group and at least one hydrophobic carbonate monomer comprising an ethyl, a propyl, and/or a butyl functionality.

Following is a description of an exemplary antiviral polymer comprising an aliphatic polycarbonate backbone, a single sulfonate functionality, and a single n-butyl functionality. It is to be understood that the antiviral polymer could be prepared with more than one sulfonate or butyl functional group and that the n-butyl functionality could be replaced with an alkyl group as described herein.

Formulas (I)-(III) show the synthesis of monomers that comprise the antiviral polymers as described herein: Formula (I) shows the synthesis of a protected sulfonate-functionalized alcohol (Example 1), which is reacted with a cyclic carbonate monomer (MTC) to form the protected sulfonate-functionalized cyclic carbonate monomer of Formula (II) (MTC-OPS) (Example 2). Formula (III) shows the synthesis of a cyclic carbonate monomer functionalized with an n-butyl group (MTC-OBu) (Example 3). The antiviral polymers are formed by reacting the monomers of Formulas (II) and (III) to form copolymers functionalized with sulfonate and n-butyl groups where the sulfonate functionality is a water-soluble group and the n-butyl functionality is a water-insoluble hydrocarbon chain.

(I)

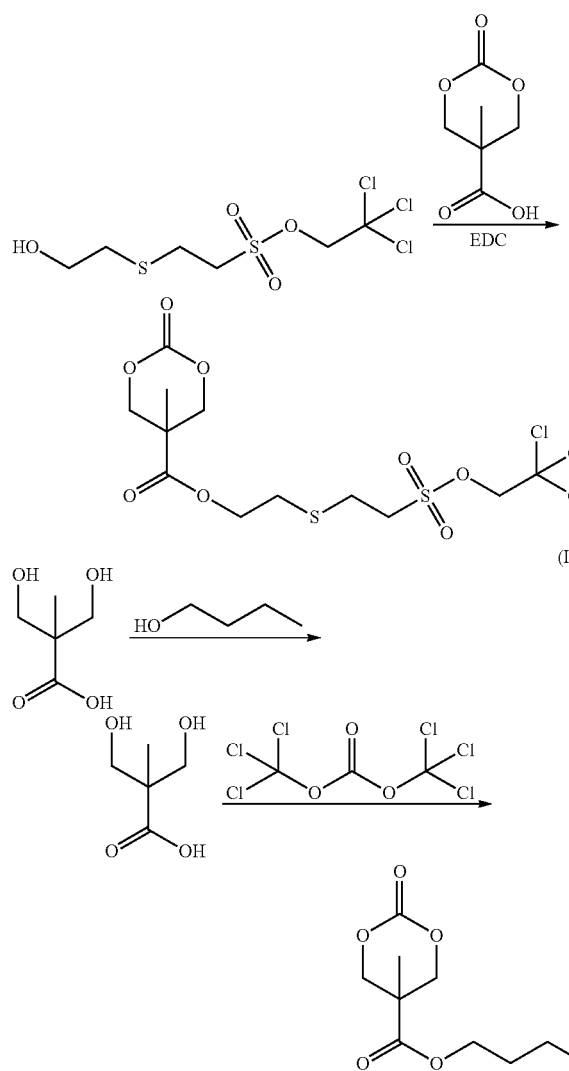

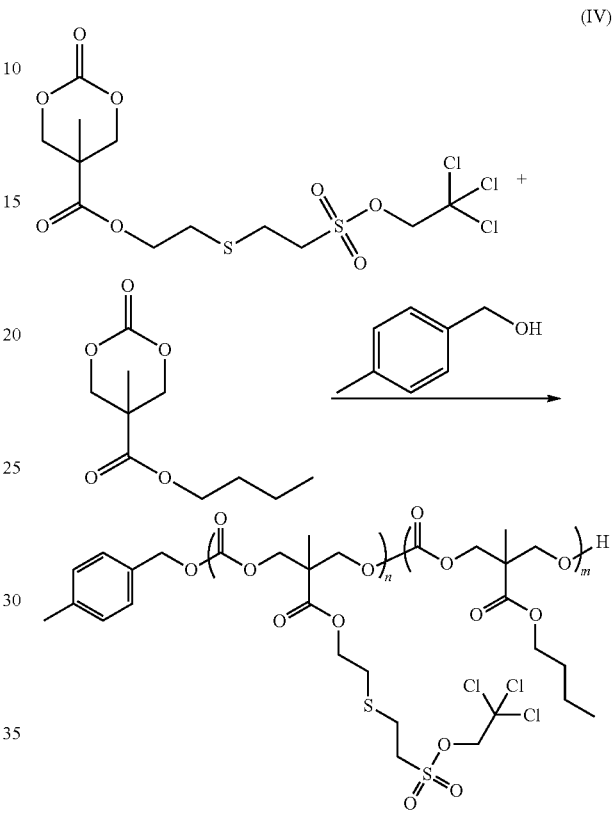

As described in Example 4, three separate copolymers were synthesized with sulfonate and n-butyl functional groups and a total degree of polymerization of around 20 with varying sulfonate content (30, 50 and 80 mol %). The polymerizations were conducted using a trichloroethanol (TCE)-protected sulfonate cyclic carbonate and n-butyl functionalized cyclic carbonate via organo-catalyzed ring opening polymerization as shown in Formula (IV).

As described in Example 5, the TCE-protected groups of the three copolymers were removed under mild reductive conditions using zinc in the presence of acetic acid. After deprotection, the n-butyl functionalized sulfonate copolymers were dialyzed against a solution of NaCl first, in order to remove any trace of $Zn^{2+}$ as counter-ion, followed by dialysis against distilled water. The deprotection process for the TCE-protected copolymers is shown in Formula (V).

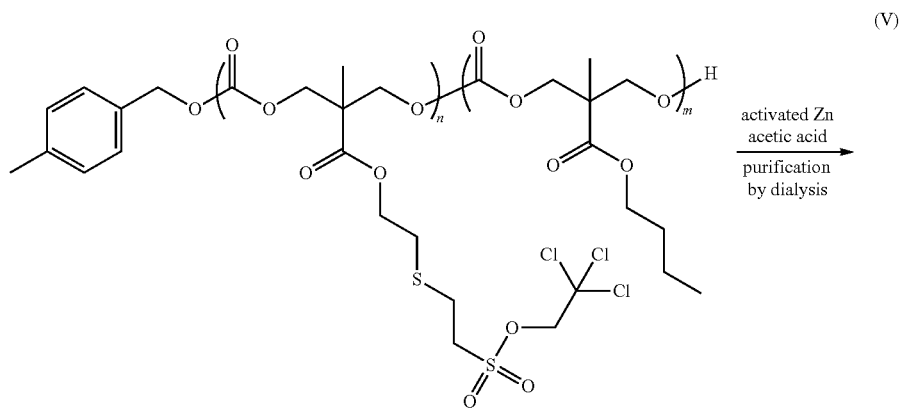

-continued

The six copolymers produced in Examples 4 and 5 were named as follows according to their sulfonate content and the presence of the protecting group TCE: $pS30^{TCE}$, $pS50^{TCE}$, and $pS80^{TCE}$ for the protected copolymers; and pS30, pS50, and pS80 for the deprotected copolymers. TABLE 1 provides characteristics of the TCE-protected copolymers and TABLE 2 provides characteristics of the deprotected copolymers.

Figure 8:
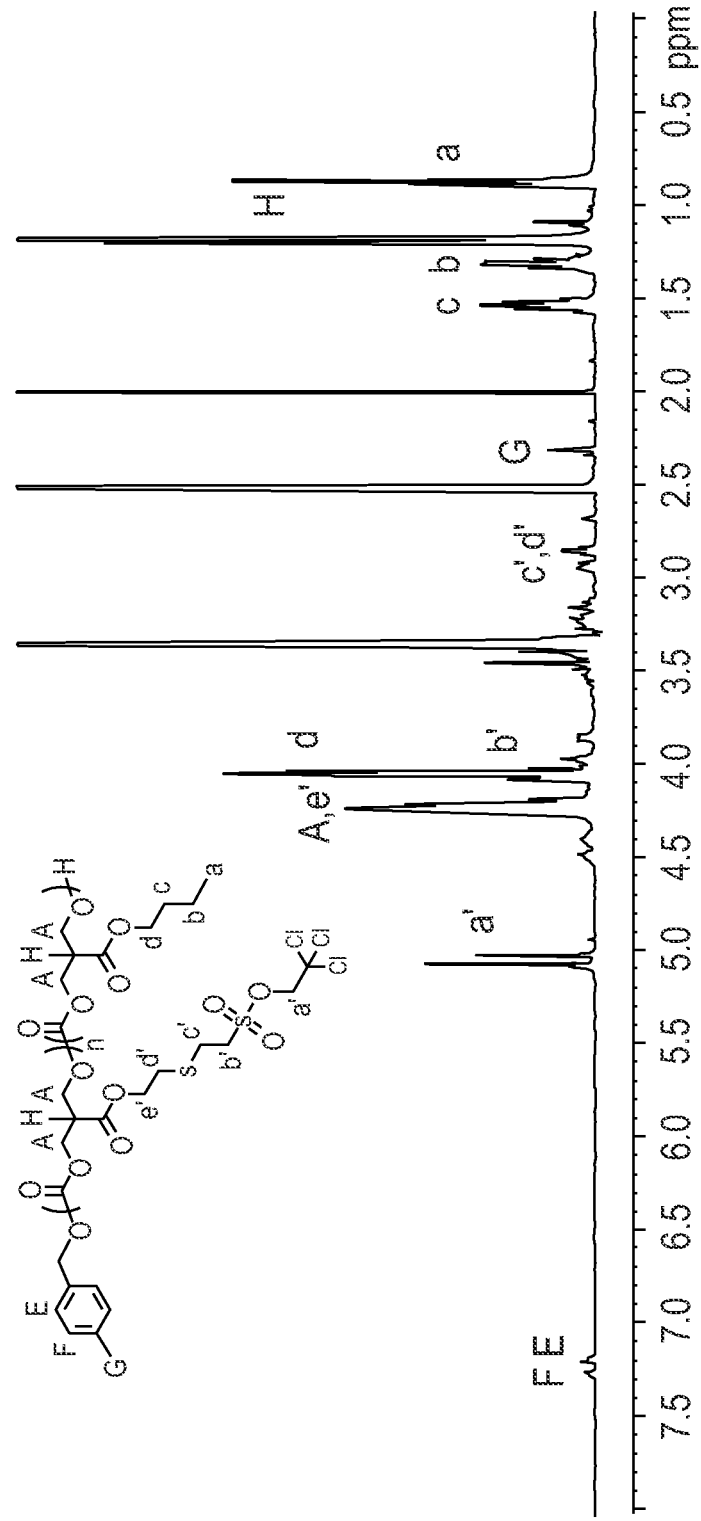
FIG. 8 is the $^1$H NMR spectrum of trichloroethanol (TCE)-protected pS30 (pS30$^{TCE}$) in deuterated dimethyl sulfoxide (DMSO-d$_6$).
Figure 9:
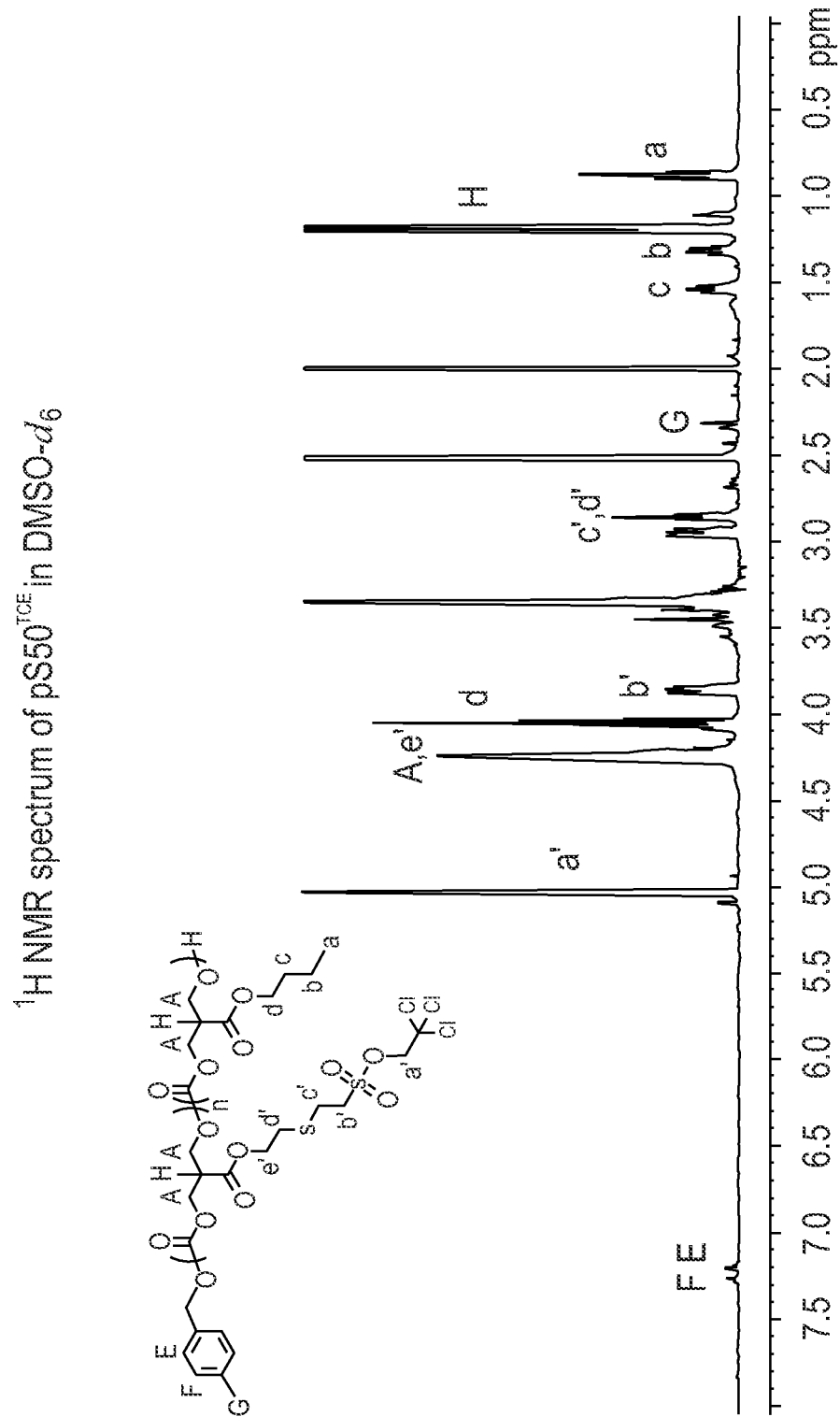
FIG. 9 is an $^1$H NMR spectrum of TCE-protected pS50 (pS50$^{TCE}$) in DMSO-d$_6$.
Figure 10:
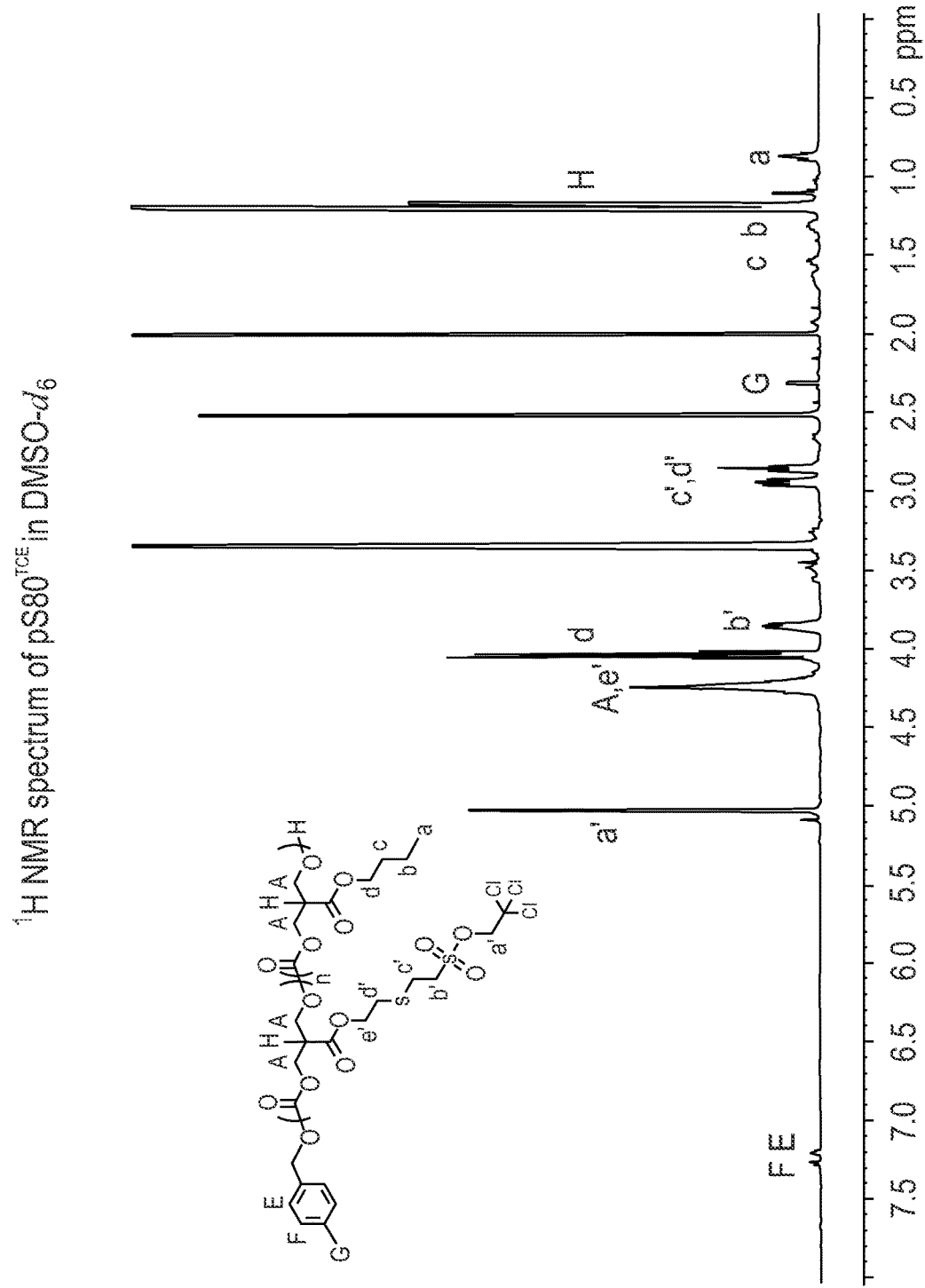
FIG. 10 is an $^1$H NMR spectrum of TCE-protected pS80 (pS80$^{TCE}$) in DMSO-d$_6$.

The cytotoxicity of the deprotected sulfonated polycarbonate polymers towards a mammalian cell line was tested in order to establish the biocompatibility of the antiviral agents on living tissue. As described in Example 6, the toxicity of the three deprotected polymers against HepG2-NTCP (human heptomacells, HepG2, expressing sodium taurochlorate cotransporting polypeptide, NTCP) was assessed over the course of 24 hours. As shown in FIG. 1 and TABLE 2, all three sulfonated copolymers (pS30, pS50, and pS80) exhibited a low cytotoxicity ($IC_{50}$>450 µg/mL) thus confirming their biocompatibility as an antiviral agent for human and/or animal use. TABLE 2 also shows that the $IC_{50}$ cell viability values decreased with decreasing sulfonate content; the pS30 polymer having an $IC_{50}$ of 470 µg/mL, the pS50 polymer having an $IC_{50}$ of 770 µg/mL, and the pS80 polymer having an $IC_{50}$ of 930 µg/mL. Reference to FIGS. 8-10 shows that the n-butyl content ($^1$H NMR spikes a-d) of the polymers is inversely proportional to the sulfonate content with the pS30 polymer having the highest n-butyl content, the pS80 polymer having the lowest n-butyl content, and the pS50 polymer having an n-butyl content that falls between that of the other two polymers. Because the $IC_{50}$ values of the deprotected polymers decreased with increased hydrophobicity (as indicated by n-butyl content), it follows that the hydrophobicity of the polymers influenced the cell viability. While not intending to be bound by theory, the increased hydrophobicity of the polymers likely caused an increase in cell cytotoxicity as a result of an increase in cell membrane disruption.

Figure 2:
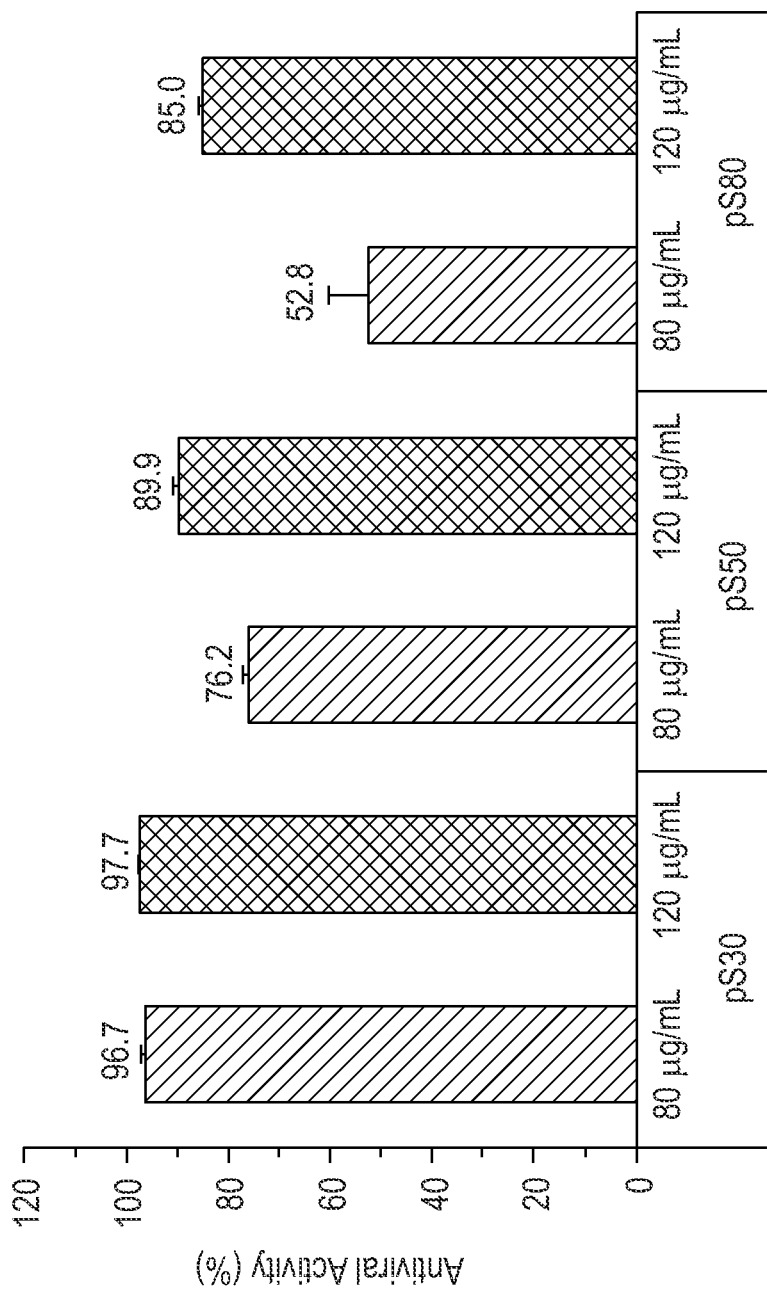
FIG. 2 is a graph showing antiviral activity of pS30, pS50, and pS80 at 80 µg/mL and 120 µg/mL.
Figure 3:
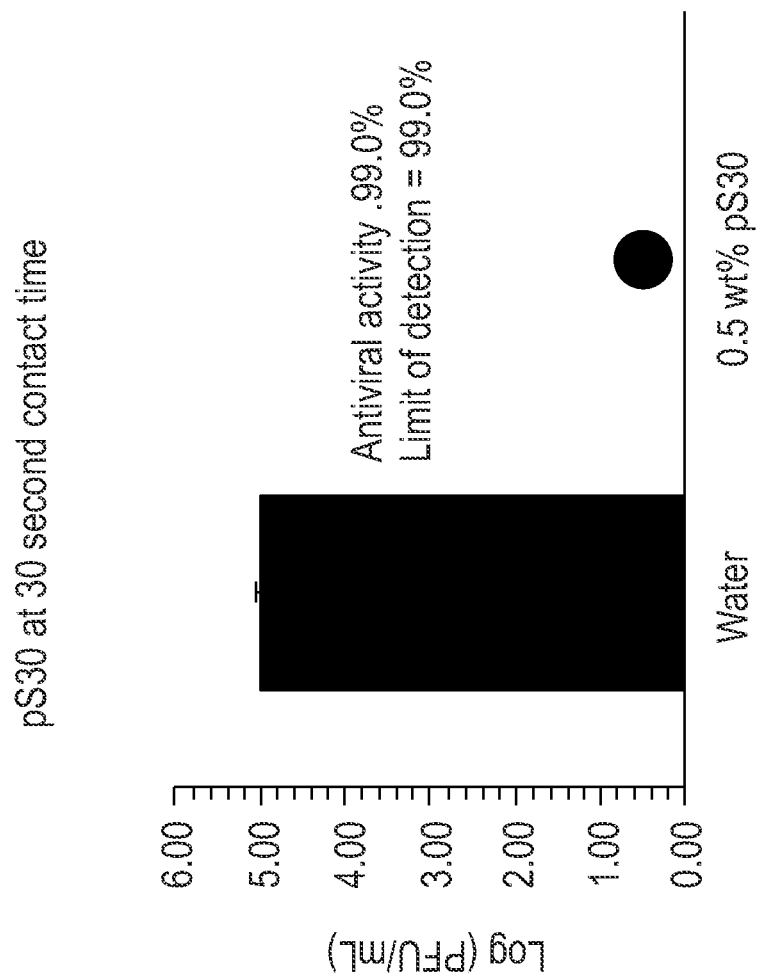
FIG. 3 is a graph showing that pS30 killed off all coronavirus viral particles within 30 seconds of treatment.

Mouse hepatitis virus (MHV) is a highly infectious type of coronavirus which has been extensively studied and seems to share a number of similarities with severe acute respiratory syndrome coronavirus 2 (SARS-CoV-2); thus, MHV is a suitable model for a preliminary screening of active antiviral compounds. As described in Example 7, the deprotected polymers deactivated MHV at concentrations of 80 µg/mL and 120 µg/mL in a dose-dependent manner. As shown in FIG. 2, the antiviral activity of all three polymers increased when the concentration of the polymers was increased from 80 µg/mL to 120 µg/mL. The pS80 polymer showed the largest increase in antiviral activity jumping from 52.8% for the 80 µg/mL to 85% for the 120 µg/mL treatment. The pS50 polymer increased from 76.2% antiviral activity at 80 µg/mL to 89.9% antiviral activity at 120 µg/mL Of the three polymers, the pS30 polymer was the most effective showing antiviral activity of 96.7% at 80 µg/mL and a slightly higher antiviral activity of 97.7% at 120 µg/mL. FIG. 3 shows that the pS30 polymer at a concentration of 5 mg/mL completely eliminated the MHV virus within 30 seconds. The data of FIGS. 2, 3, and TABLE 2 indicate that the antiviral activity of the deprotected polymers correlates with the hydrophobicity of the polymers. For example, the pS30 polymer, which is the most effective polymer, is also the most hydrophobic as evidenced by the high n-butyl content in that polymer. The antiviral and cell viability properties of the sulfonated polycarbonate polymers described herein are thus dependent on the hydrophobicity of the polymers. To ensure maximal antiviral activity and cell viability, the sulfonated polycarbonate polymers are tunable by altering the hydrophilic and hydrophobic functionalities.

The antiviral agents have applicability as an antiviral medicine for administration to a human or animal or as an environmental antiviral sanitization agent. The biocompatible and biodegradable antiviral polymers described herein may be administered to a human or animal through any route including, without limitation, intravenous, intradermal, intranasal, and/or oral. As an environmental antiviral sanitization agent, the antiviral agent may be in the form of, for example, an air sanitizing spray, a sanitizing spray for surfaces, or a hand sanitizing gel.

The descriptions of the various aspects and/or embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the aspects and/or embodiments, the practical application or technical improvement over technologies found in the marketplace, or to enable others of ordinary skill in the art to understand the aspects and/or embodiments disclosed herein.

EXPERIMENTAL

The following examples are set forth to provide those of ordinary skill in the art with a complete disclosure of how to make and use the aspects and embodiments of the invention as set forth herein. While efforts have been made to ensure accuracy with respect to variables such as amounts, temperature, etc., experimental error and deviations should be considered. Unless indicated otherwise, parts are parts by weight, temperature is degrees centigrade, and pressure is at or near atmospheric. All components were obtained commercially unless otherwise indicated.

The following materials and procedures were used in the Examples that follow.

POLYMER SYNTHESIS: All polymerization reactions were conducted in a glovebox filled with nitrogen.

MATERIALS: 1,8-diazabicyclo[5.4.0]undec-7-ene (DBU) was distilled from $CaH_2$ under dry $N_2$ and transferred to a glove box. N-(3,5-trifluoromethyl)phenyl-N'-cyclohexylthiourea (TU) catalyst and 5-methyl-5-carboxyl-1,3-dioxan-2-one (MTC-OH) (Formula II) were prepared as described in the literature (Pratt et al., Macromolecules 39:7863-7871 (2006) & Tan et al., Macromolecules 54:1767-1774 (2021)). Before transferring into the glovebox, monomers and other reagents were dried extensively by freeze-drying under high vacuum.

NUCLEAR MAGNETIC RESONANCE (NMR) SPECTROSCOPY: $^1H$ and $^{13}C$ NMR spectra of monomers and polymers were recorded using a Bruker Advance 400 spectrometer, (Bruker Corporation, Billerica, MA, USA) and operated at 400 and 100 MHz, respectively. The solvent proton/carbon signal was used as the internal reference standard.

MOLECULAR WEIGHT DETERMINATION BY SIZE EXCLUSION CHROMATOGRAPHY (SEC): SEC was recorded on a Waters 2695D Separation Module (Waters Corporation, Milford, MA, USA) equipped with an OPTILAB® rEX differential refractometer (Wyatt Technology Corporation, Coleta, CA USA) and Waters HR-4E column (Waters Corporation, Milford, MA, USA). The system was equilibrated at 30° C. in THF, which served as the polymer solvent and eluent with a flow rate of 1.0 mL/min, with an injection volume of 100 µL. Data collection and analysis were performed using Astra software (version 5.3.4.14) (Wyatt Technology Corporation, Goleta, CA, USA, version 5.3.4.14). The columns were calibrated with a series of polystyrene standards ranging from $M_p$=360 Da to $M_p$=778 kDa (Polymer Standard Service—USA Inc., Amherst, MA, USA).

Example 1

Synthesis of Tricholorethanol (TCE)-Protected Sulfonate-Functionalized Alcohol

In a 250 mL round-bottom flask flushed with nitrogen ($N_2$), 100 mL of tetrahydrofuran (THF) was placed in an ice bath. 2.30 mL of trichloroethanol (TCE) (23.9 mmol, 1.2 eq) and 8.32 mL of triethylamine (TEA) (59.7 mmol, 3 eq) were added to the solution. After leaving the solution to cool down for 10 minutes, 1.99 mL of 2-chloroethansulfonyl chloride (19.9 mmol, 1 eq) was added dropwise with a syringe. After 2 hours, 1.68 mL of mercaptoethanol (23.9 mmol, 1.2 eq) was added to the reaction mixture, which was left to stir overnight. The TEA salt was removed by filtration using a thin silica plug. The solvent was removed using a rotary evaporator to obtain a brown oil. The crude product was purified using a flash chromatography column with ethyl acetate (EtOAc) and hexane as eluent. A clear oil was obtained with 70% yield (4.37 g).

The synthesis of the protected sulfonate-functionalized alcohol is shown schematically above in Formula (I).

$^1H$ NMR (400 MHz, 298 K, $CDCl_3$, δ): 4.75 (s, 2H), 3.81 (t, J=5.36 Hz, 2H), 3.58 (m, 2H), 3.07 (m, 2H), 2.79 (t, J=5.8 Hz, 2H).

$^{13}C$ NMR (400 MHz, 298 K, $CDCl_3$, δ): 93.44, 61.11, 52.00, 35.40, 25.25.

Example 2

Synthesis of TCE-Protected Sulfonate (PS)-Functionalized Cyclic Carbonate Monomer (MTC-OPS)

In a 250 mL round-bottom flask placed in an ice bath and flushed with $N_2$, 0.966 g of MTC-OH (5-methyl-5-carboxyl-1,3-dioxan-2-one prepared as described above) (1.5 eq) and 1.277 g (1 eq) of the protected sulfonate alcohol of Example 1 were dissolved in 60 mL of dry dichloromethane (DCM) with 0.049 g of 4-dimethylaminopyridine (DMAP) (0.1 eq). A solution of 1.156 g of 1-ethyl-3-(3-dimethylaminopropyl) carbodiimide hydrochloride (EDC-HCl) (1.5 eq) was prepared in 40 mL of DCM and added dropwise to the reaction mixture. Upon completion of the addition, the reaction mixture was left to stir overnight. The solvent was removed and the crude product was purified using a flash chromatography column with EtOAc and hexane as eluents to obtain MTC-OPS as a clear oil (1.728 g, 94% yield).

Figure 4:
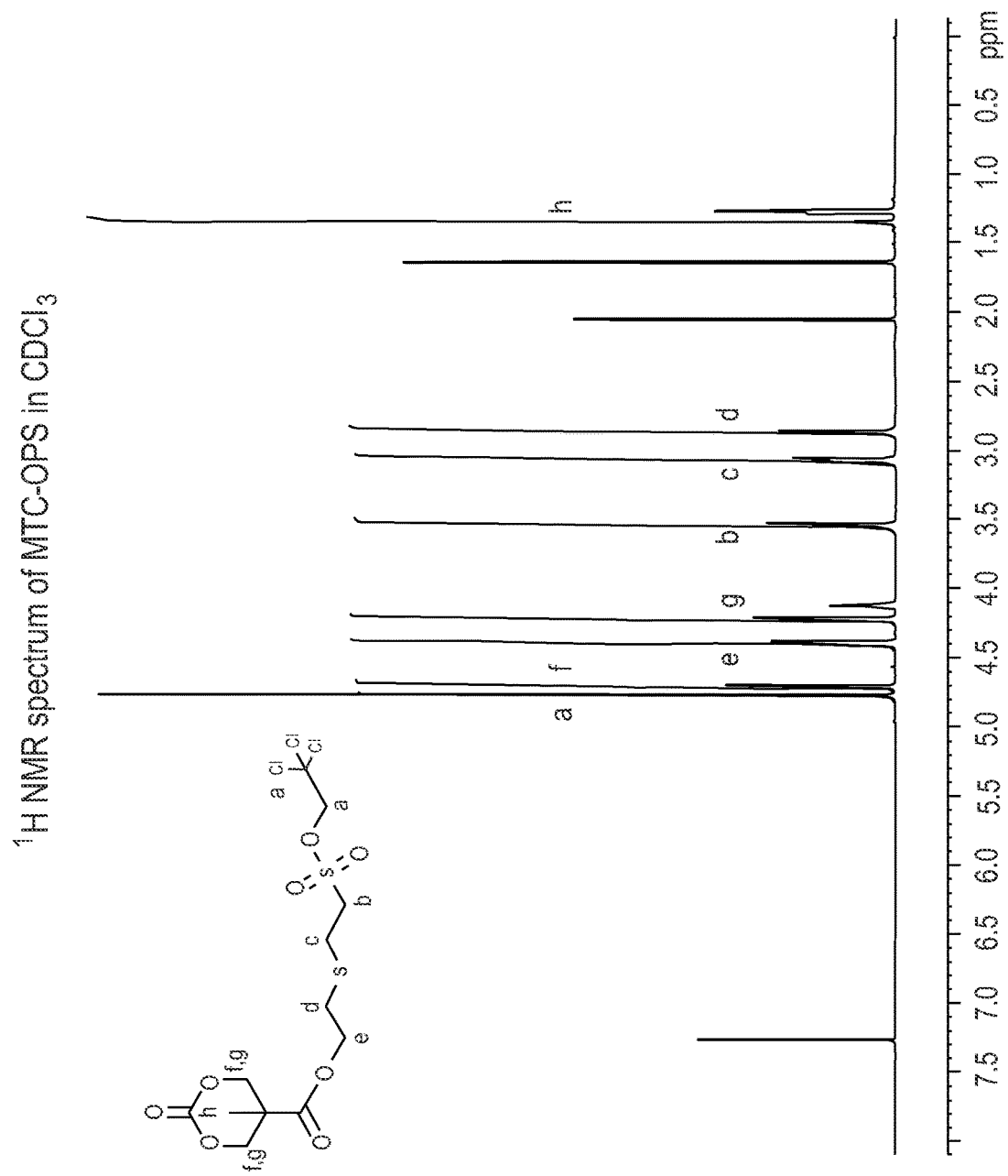
FIG. 4 is an $^1$H NMR spectrum of the protected sulfonate (PS)-functionalized cyclic carbonate monomer (MTC-OPS) in deuterated chloroform (CDCl$_3$).
Figure 5:
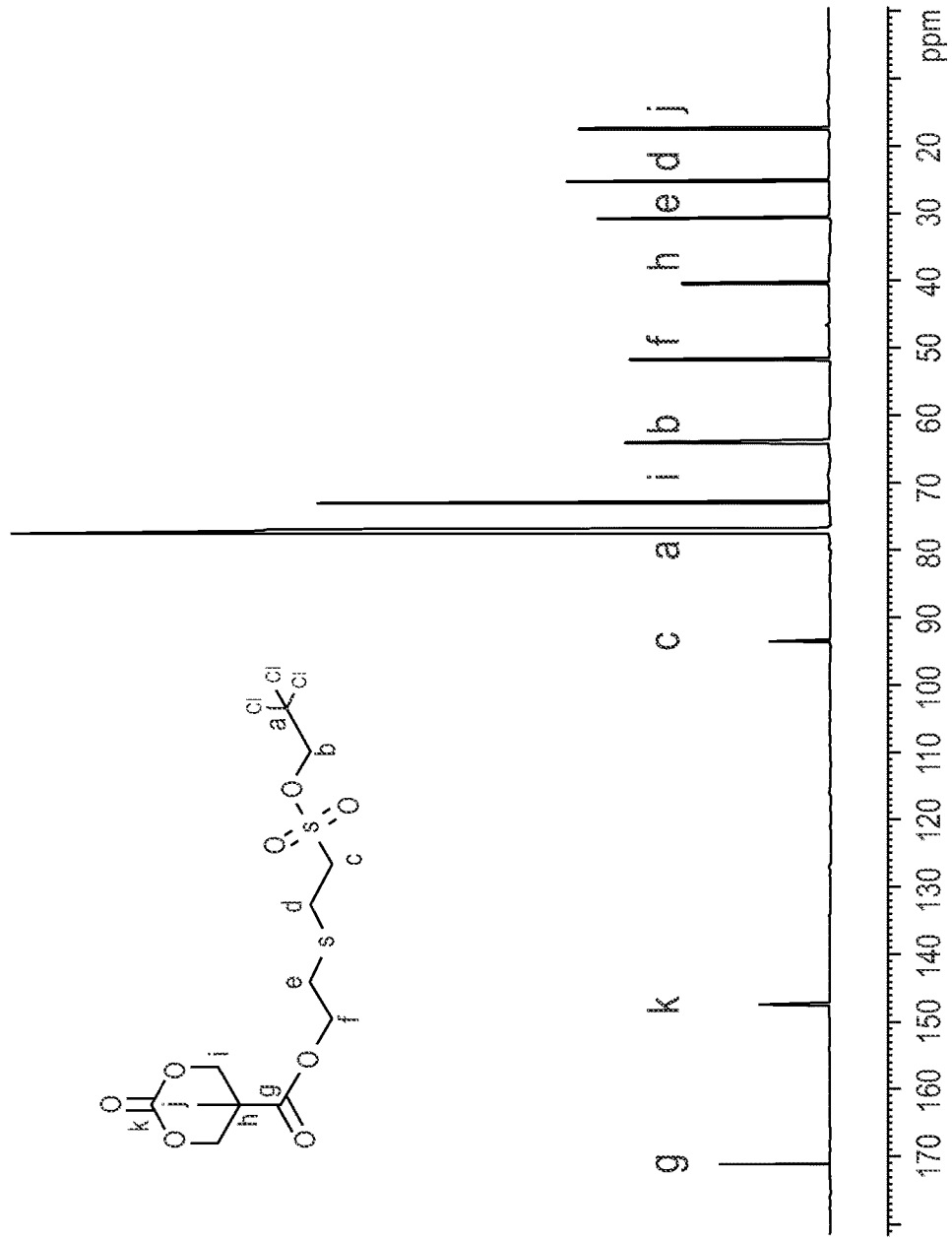
FIG. 5 is a $^{13}$C NMR spectrum of MTC-OPS in CDCl$_3$.

The synthesis of MTC-OPS is shown schematically above in Formula (II). FIG. 4 shows the $^1H$ NMR spectrum of the MTC-OPS in deuterated chloroform ($CDCl_3$) and FIG. 5 shows the $^{13}C$ NMR spectrum of the MTC-OPS in $CDCl_3$.

$^1H$ NMR (400 MHz, $CDCl_3$) 4.79 (s, 2H), 4.70 (d, J=10.96 Hz, 2H), 4.39 (t, J=6.48 Hz, 2H), 4.21 (d, J=10.92 Hz, 2H), 3.54 (m, 2H), 3.06 (m, 2H), 2.86 (t, J=6.48 Hz, 2H), 1.34 (s, 3H).

$^{13}C$ NMR (400 MHz, 298 K, $CDCl_3$, δ): 171.1 (—(C=O)—O—$C_2H_4$—S—), 147.4 (—O—(C=O)—O—), 93.5 (—$CH_2$—$SO_2$—O—), 77.3 (—$CCl_3$), 73.0 (—O—(C=O)—O—$CH_2$—), 63.9 (—$CH_2$—$CCl_3$), 51.6 (—(C=O)—O—$CH_2$—$CH_2$—S—), 40.4 (—C($CH_3$)—(C=O)—O—$C_2H_4$—S—), 30.7 (—(C=O)—O—$CH_2$—$CH_2$—S—), 25.16 (—S—$CH_2$—$CH_2$—$SO_2$—O—), 17.5 (—C($CH_3$)—(C=O)—O—$C_2H_4$—S—).

Example 3

SYNTHESIS OF TCE-PROTECTED N-BUTYL FUNCTIONALIZED CYCLIC CARBONATE MONOMER (MTC-OBu)

4.426 g of bisMPA (33 mmol, 1 eq) was dissolved in 50 mL of n-butanol with 1.50 g of Amberlyst-15. The mixture was refluxed overnight. The residue was filtered out and the solvent was removed by vacuum distillation. 40 mL of DCM was added to the resulting viscous liquid to filtrate the unreacted reagents. The solution was dried over $MgSO_4$, filtered, and the solvent removed to yield 5.25 g of clear liquid (27.6 mmol, 84% yield).

2.81 g of triphosgene (9.46 mmol, 1 eq) in 30 mL of DCM was added dropwise to a solution of 3.60 g of the bishydroxyl intermediate (18.92 mmol, 2 eq) and 9.20 mL of pyridine (113.54 mmol, 12 eq) in 30 mL of DCM over 30 min at −75° C. using a dry ice and acetone bath under nitrogen atmosphere. The reaction mixture was left to stir for 2 hrs under chilled conditions, then allowed to reach RT. The reaction was quenched by addition of 30 mL of saturated $NH_4Cl$, followed by washes of the organic phase with 3×50 mL of 1M HCl and 1×50 mL of saturated $NaHCO_3$. The organic phase was dried over MgSO$_4$, filtered, and the solvent removed under vacuum to obtain MTC-OBu as a clear oil (1.819 g, 8.41 mmol, 89% yield).

Figure 6:
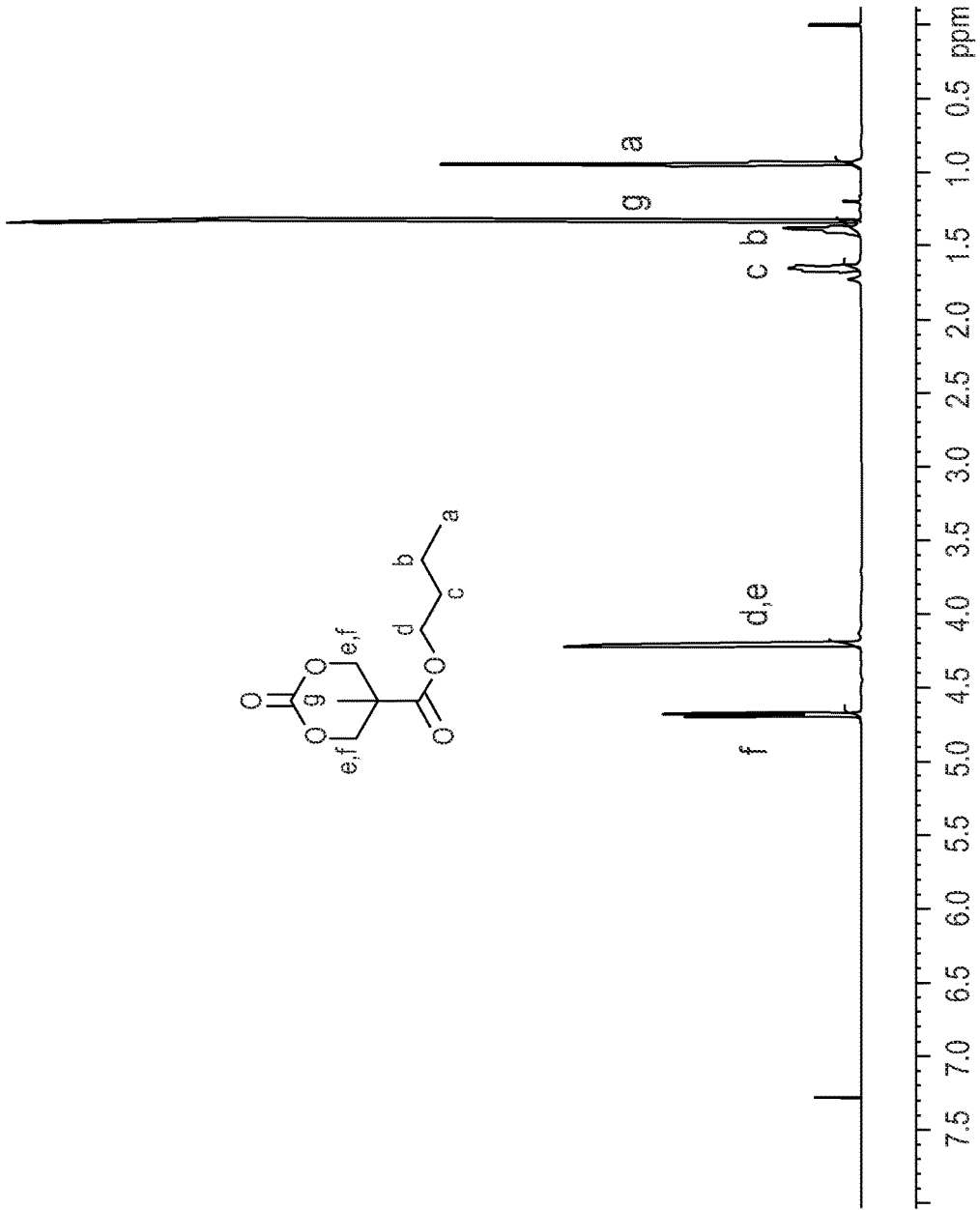
FIG. 6 is an $^1$H NMR spectrum of the n-butyl functionalized cyclic carbonate monomer (MTC-OBu) in CDCl$_3$.
Figure 7:
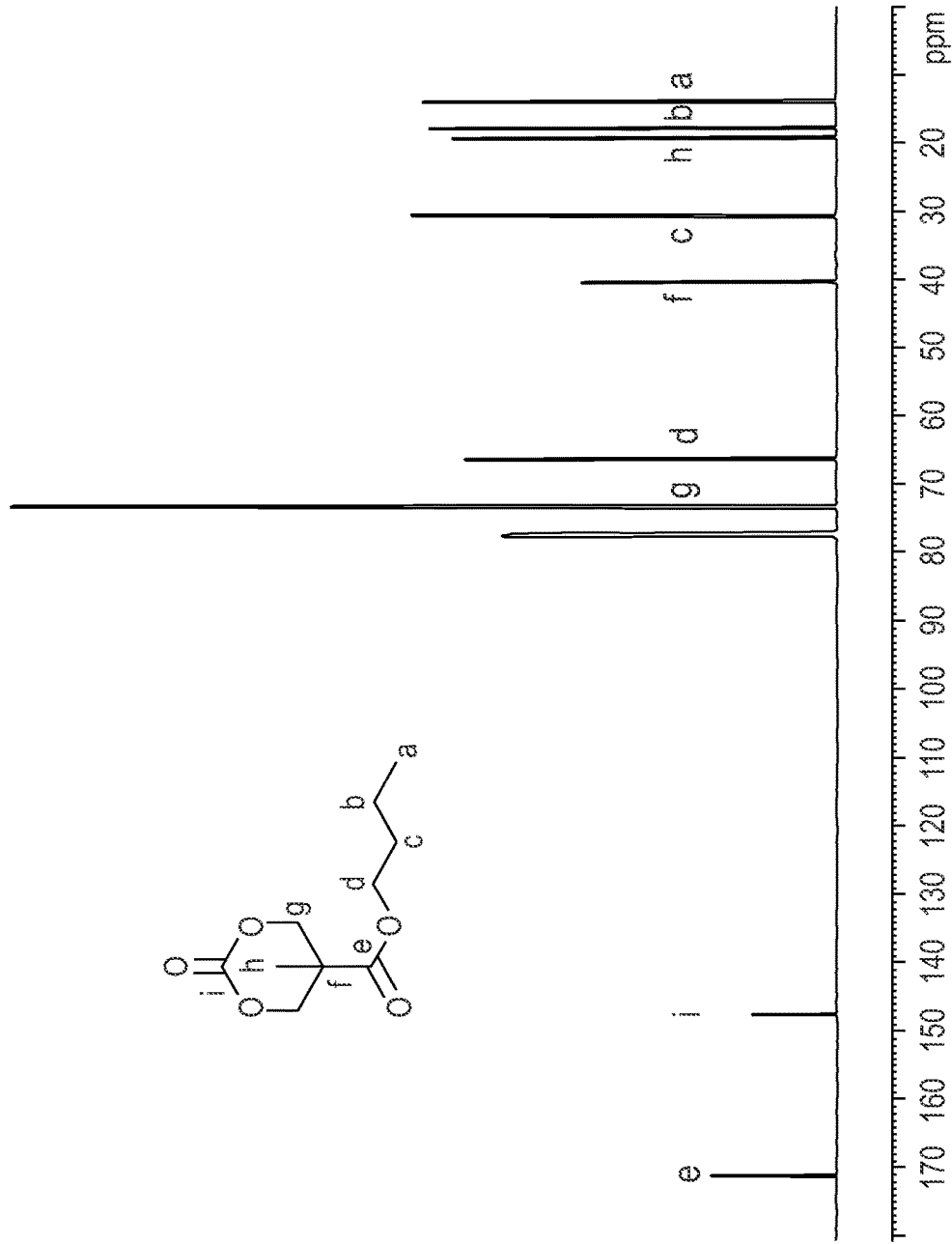
FIG. 7 is a $^{13}$C NMR spectrum of MTC-OBu in CDCl$_3$.

The synthesis of MTC-OBu is shown schematically above in Formula (III). FIG. 6 shows the $^1$H NMR spectrum of the MTC-OBu in CDCl$_3$ and FIG. 7 shows the $^{13}$C NMR spectrum of the MTC-OBu in CDCl$_3$.

$^1$H NMR (400 MHz, CDCl$_3$) 4.69 (d, J=10.88 Hz, 2H), 4.21 (t, J=10.84 Hz, 2H), 4.19 (d, J=6.64 Hz, 2H), 1.65 (m, 2H), 1.39 (m, 2H), 1.35 (s, 3H), 0.95 (t, J=7.40 Hz, 3H).

$^{13}$C NMR (400 MHz, 298 K, CDCl$_3$, δ): 171.2 (—(C=O)—O—C$_4$H$_9$), 147.6 (—O—(C=O)—O—), 73.0 (—O—(C=O)—O—CH$_2$—), 66.1 (—(C=O)—O—CH$_2$—C$_3$H$_7$), 40.2 (—C(CH$_3$)—(C=O)—O—C$_4$H$_9$), 30.5 (—(C=O)—O—CH$_2$—CH$_2$—C$_2$H$_5$), 19.0 (—C(CH$_3$)—(C=O)—O—C$_4$H$_9$), 17.6 ((—(C=O)—O—C$_2$H$_4$—CH$_2$—CH$_3$), 13.6 (—(C=O)—O—C$_3$H$_6$—CH$_3$).

Example 4

Synthesis of TCE-Protected N-Butyl Functionalized Sulfonate Polymers

In a 25-mL vial equipped with a magnetic stir bar, 235.2 mg of MTC-OBu (1.088 mmol, 16 eq), 500.0 mg of MTC-OPS (1.088 mmol, 16 eq), and 25.2 mg of TU (0.068 mmol, 1 eq) were dissolved in 7 mL of dry DCM. 8.3 mg of 4-mercaptobenzoic acid (4-MBA) (0.068 mmol, 1 eq), followed by 10.2 µL of DBU (0.068 mmol, 1 eq) were added to the solution to initiate the polymerization. The reaction mixture was left to stir at room temperature for 30 min, then quenched by the addition of excess benzoic acid (~25 mg). After polymerization, the crude polymer was purified and any residual monomer remaining in the reaction mixture was removed using a SEPHADEX® (Cytiva Bioprocess R&D AB, Uppsala, SE) size exclusion column with THF as eluent.

Using the procedures from Examples 1-4, three TCE-protected n-butyl functionalized sulfonate polymers were prepared and named as follows according to their sulfonate content and the presence of the TCE protecting group: pS30$^{TCE}$, pS50$^{TCE}$, and pS80$^{TCE}$. TABLE 1 provides characteristics of the TCE-protected polymers. The synthesis reaction for the TCE-protected polymers is shown schematically above in Formula (IV). FIG. 8 shows the $^1$H NMR spectrum of pS30$^{TCE}$ in deuterated dimethyl sulfoxide (DMSO-d$_6$); FIG. 9 shows the $^1$H NMR spectrum of pS50$^{TCE}$ in DMSO-d$_6$; and FIG. 10 shows the $^1$H NMR spectrum of pS80$^{TCE}$ in DMSO-d$_6$.

TABLE 1

TCE PROTECTED POLYMERS

| Sample Name | Protected sulfonate content %[a] | Degree of polymerization Dp[a] | Weight average molecular weight (g/mol) M$_{th}$[a] | Number average molecular weight (g/mol) M$_n$[b] | Dispersity Đ[b] |
|---|---|---|---|---|---|
| pS30$^{TCE}$ | 30 | 20 | 5900 | 5300 | 1.18 |
| pS50$^{TCE}$ | 50 | 19 | 6670 | 5100 | 1.18 |
| pS80$^{TCE}$ | 80 | 14 | 5830 | 4600 | 1.18 |

[a]%, Dp, and M$_{th}$ were determined by $^1$H NMR.
[b]M$_n$ and Đ were determined by SEC/RI (refractive index) in THF using polystyrene as molecular weight standards.

Example 5

Post-Polymerization Removal of the TCE-Protecting Groups from the N-Butyl Functionalized Sulfonate Polymers 300 mg of the individual polymers was dissolved in 12 mL of THF and 6 mL of MeOH. 2 mL of acetic acid (glacial) and 200 mg of activated zinc powder were added to the solution, which was left to stir at RT for 1 hr. The solution was subsequently filtered and the solvent removed under vacuum. 10 mL of 1M HCl was introduced in order to acidify the solution. The polymers were purified by dialysis using a membrane with a 2 kDa cut-off.

Figure 11:
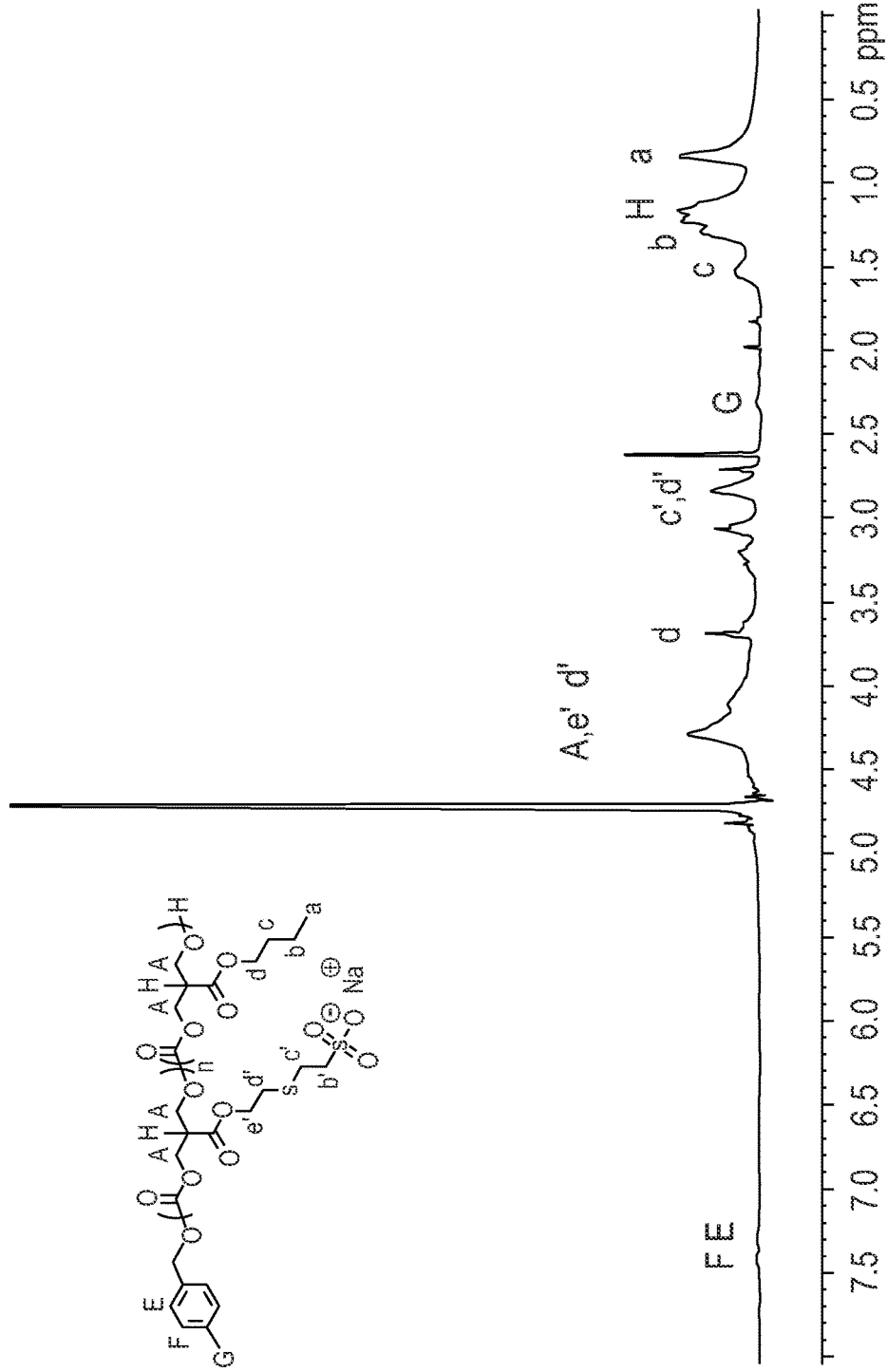
FIG. 11 is an $^1$H NMR spectrum of pS50 in deuterated water (D$_2$O).

Using the procedures from Examples 1-5, three deprotected n-butyl functionalized sulfonate polymers were prepared and named as follows according to their sulfonate content: pS30, pS50, and pS80. TABLE 2 provides characteristics of the deprotected polymers. The synthesis reaction for the deprotection of the polymers is shown schematically above in Formula (V). FIG. 11 shows the $^1$H NMR spectrum of pS50 in deuterated water (D$_2$O).

TABLE 2

DEPROTECTED POLYMERS

| Sample Name | Sulfonate content (%) | Degree of polymerization Dp | Weight average molecular weight (g/mol) M$_{th}$[a] | Half-maximal inhibitory Concentration (µg/mL) IC$_{50}$[b] |
|---|---|---|---|---|
| pS30 | 30 | 20 | 4030 | 470 |
| pS50 | 50 | 19 | 4690 | 770 |
| pS80 | 80 | 14 | 4370 | 930 |

[a]M$_{th}$ was determined by $^1$H NMR.
[b]IC$_{50}$ was determined as the concentration at which cell viability was inhibited by 50% relative to the positive control by in vitro cell viability assessment.

Example 6

Cell Viability Assessment of the Deprotected Polymers on HEPG2-NTCP Cells

Human hepatocyte HepG2-NTCP cells were seeded at a density of 8×10$^4$ cells per well onto a 96-well plate and incubated at 37° C. for 36 hours. To treat the cells, the spent medium was removed and 100 µL of polymer solution in fresh medium was added to each well. Subsequently, the cells were incubated at 37° C. for 24 hours and cell viability was determined using the ALAMARBLUE® cell viability reagent (Trek Diagnostic Systems LLC, Cleveland, OH, USA). The results of the cell viability assessment are shown in FIG. 1.

Example 7

Anti-Murine Hepatitis Virus (MHV) Activity Assay

To test the antiviral activity of the deprotected polymers at low concentrations for 30 min at 37° C., the individual pS30, pS50, and pS80 polymers were dissolved in DI water to concentrations of 80 µg/mL and 120 µg/mL. 950 µL of polymer solution was mixed with 50 µL of murine hepatitis virus A59 (MHV-A59) (~10$^7$ PFU/mL) and incubated in a 37° C. for 30 min. After 30 min, 100 µL of the viral and polymer mixture was taken out and diluted in 900 µL of DME2 (DMEM supplemented with 2% horse serum). The solutions were further diluted serially to 1/1,000 and 1/10,000 the original concentration. As a control, 950 μL of water was mixed with 50 μL of MHV-A59 and subjected to the same treatments as outlined above. The results of the dose dependent antiviral activity assay for all three polymers at 80 μg/mL and 120 μg/mL is shown in FIG. 2.

To test the antiviral activity of the deprotected polymers at high concentration for 30 s, the individual pS30, pS50, and pS80 polymers were dissolved in DI water to a concentration of 5 mg/mL (equivalent to 0.5 w/v %). 950 μL of polymer solution was mixed with 50 μL of MHV-A59 (~$10^7$ PFU/mL). The solutions were mixed by pipetting for 30 s, then 100 μL of the viral and polymer mixture was taken out and diluted in 900 μL of DME2. The solutions were further diluted serially to 1/1,000 and 1/10,000 the original concentration. As a control, 950 μL of water was mixed with 50 μL of MHV-A59 and subjected to the same treatments as outlined above. The results of the antiviral activity assay for the pS30 polymer at 5 mg/mL concentration is shown in FIG. 3. As shown therein, the pS30 polymer killed all of the MHV-59 virus within 30 seconds of application.

Viral titers were quantified by a plaque assay with NCTC 1469 cells (neonatal mouse liver cells) serving as the host for the plaque assay. To perform the assay, 1.2-million cells were seeded overnight on 6-well plates. Prior to viral adsorption, the cells were washed with PBS. Next, 500 μL of viral sample was incubated with the cells for 1 h at 37° C. with intermittent shaking. After 1 h, a warm mixture of DME2 and agarose (final concentration 0.8 w/v %) was added to each of the wells. The well plates were incubated at 37° C. for 2 days before they were fixed with neutral buffered formalin and stained with crystal violet.

We claim:

1. A composition comprising a water-soluble polymer with an aliphatic polycarbonate backbone, a first carbonate monomer with at least one hydrophilic sulfonate group; and a second carbonate monomer with at least one hydrophobic alkyl group.

2. The composition of claim 1, wherein the alkyl group is selected from a group consisting of: an ethyl group, a propyl group, and a butyl group.

3. The composition of claim 1, wherein the water-soluble polymer is a biocompatible and biodegradable anti-viral agent.

4. The composition of claim 1, wherein an anti-viral potency of the water-soluble polymer is tunable by altering the concentrations of the at least one hydrophilic sulfonate group and the at least one hydrophobic alkyl group.

5. A composition comprising a water-soluble polymer with an aliphatic polycarbonate backbone, at least one carbonate monomer with a hydrophilic sulfonate group, and at least one carbonate monomer with a hydrophobic n-butyl group.

6. The composition of claim 5, wherein the water-soluble polymer is a biocompatible and biodegradable anti-viral agent.

7. The composition of claim 5, wherein an anti-viral potency of the water-soluble polymer is tunable by altering the concentrations of the at least one hydrophilic sulfonate group and the at least one hydrophobic n-butyl group.

8. A method for inhibiting viral infections in a human or animal subject comprising:

obtaining a composition comprising a water-soluble polymer with an aliphatic polycarbonate backbone, a first carbonate monomer with at least one hydrophilic sulfonate group, and a second carbonate monomer with at least one hydrophobic n-butyl group; and administering the composition to a human and/or animal subject for inhibiting viral infections in the human and/or animal subject.

9. The method of claim 8, wherein the composition inhibits reproduction of enveloped and/or non-enveloped viral RNA in the human or animal subject.

10. The method of claim 8, wherein the composition inhibits reproduction of enveloped and/or non-enveloped viral DNA in the human or animal subject.

11. The method of claim 8, wherein the composition is not cytotoxic to cells of the human or animal subject.

12. The method of claim 8, wherein the water-soluble polymer is a biocompatible and biodegradable anti-viral agent.

13. The method of claim 12, wherein the anti-viral potency of the water-soluble polymer is tunable by altering the concentrations of the at least one hydrophilic sulfonate group and the at least one hydrophobic n-butyl group.

14. The composition of claim 1, further comprising a sulfonate content in an inclusive range of 30% to 80% and an alkyl content that is inversely related to the sulfonate content.

15. The composition of claim 1, wherein a degree of polymerization of the water-soluble polymer is in an inclusive range of 14 to 20.

16. The composition of claim 5, further comprising a sulfonate content in an inclusive range of 30% to 80% and an n-butyl content that is inversely related to the sulfonate content.

17. The composition of claim 5, wherein a degree of polymerization of the water-soluble polymer is in an inclusive range of 14 to 20.

* * * * *